(12) United States Patent
Walzman

(10) Patent No.: US 11,045,177 B2
(45) Date of Patent: Jun. 29, 2021

(54) ORIENTABLE INTRACRANIAL OCCLUSION DEVICE AND METHOD

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 0 days.

(21) Appl. No.: 16/852,488

(22) Filed: Apr. 19, 2020

(65) Prior Publication Data

US 2020/0253766 A1 Aug. 13, 2020

Related U.S. Application Data

(60) Provisional application No. 62/921,378, filed on Jun. 12, 2019.

(51) Int. Cl.
*A61F 2/95* (2013.01)
*A61B 17/00* (2006.01)
(Continued)

(52) U.S. Cl.
CPC .. *A61B 17/00234* (2013.01); *A61B 17/12113* (2013.01); *A61B 17/12118* (2013.01); *A61F 2/856* (2013.01); *A61F 2/90* (2013.01); *A61F 2/95* (2013.01); *A61F 2/954* (2013.01); *A61F 2/9517* (2020.05); *A61F 2/966* (2013.01); *A61B 17/0057* (2013.01); *A61B 17/12172* (2013.01); *A61B 2017/00292* (2013.01); *A61B 2017/1205* (2013.01); *A61B 2090/3966* (2016.02); *A61F 2002/061* (2013.01); *A61F 2002/823* (2013.01); *A61F 2230/0004* (2013.01); *A61F 2230/0017* (2013.01); *A61F 2250/0023* (2013.01); *A61F 2250/0024* (2013.01); *A61F 2250/0098* (2013.01)

(58) Field of Classification Search
CPC .... A61F 2/856; A61F 2250/0023–0024; A61F 2002/823
See application file for complete search history.

(56) References Cited

U.S. PATENT DOCUMENTS 5,019,090 A 5/1991 Pinchuk
5,071,407 A 12/1991 Termin et al.
(Continued)

FOREIGN PATENT DOCUMENTS

WO PCT/US2020/035489 9/2020
WO PCT/US2020/035017 10/2020

*Primary Examiner* — Rebecca S Preston
(74) *Attorney, Agent, or Firm* — Ryan, Mason & Lewis, LLP

(57) ABSTRACT

An orientable intravascular device having a "twelve o'clock" marker on a proximal and distal end for treating an aneurysm, including a packaging catheter with an identical fixed non-round shaped inner lumen, a pusher wire having an occlusion device releasably disposed on the distal end of said pusher wire, preloaded at a fixed circumferential orientation, with corresponding markers on the outside of said packaging catheter, a hub having an inner lumen that is shaped to marry with the outer lumen of the packaging catheter to deliver a delivery wire and occlusion stent in a predicted orientation, and maintaining such orientation as the wire and stent are advanced through said delivery catheter, and while said delivery catheter is withdrawn. Methods of using same are disclosed.

25 Claims, 10 Drawing Sheets

(51) Int. Cl.
*A61F 2/966* (2013.01)
*A61F 2/90* (2013.01)
*A61B 17/12* (2006.01)
*A61F 2/954* (2013.01)
*A61F 2/856* (2013.01)
*A61F 2/06* (2013.01)
*A61F 2/82* (2013.01)
*A61B 90/00* (2016.01)

(56) References Cited

U.S. PATENT DOCUMENTS

| | | |
|---|---|---|
| 5,221,261 A | 6/1993 | Termin et al. |
| 5,306,263 A | 4/1994 | Voda |
| 5,891,057 A | 4/1999 | Chaisson et al. |
| 6,547,760 B1 | 4/2003 | Samson et al. |
| 6,723,116 B2 | 4/2004 | Tahiri |
| 8,465,442 B2 | 6/2013 | Freed |
| 2001/0041874 A1 | 11/2001 | Reydel |
| 2002/0111666 A1* | 8/2002 | Hart ............ A61F 2/95 623/1.11 |
| 2003/0139802 A1* | 7/2003 | Wulfman ........ A61B 17/12118 623/1.15 |
| 2003/0204246 A1 | 10/2003 | Chu et al. |
| 2003/0225365 A1 | 12/2003 | Greff et al. |
| 2005/0049607 A1 | 3/2005 | Hart et al. |
| 2005/0049609 A1* | 3/2005 | Gunderson ........... A61F 2/95 606/108 |
| 2006/0229657 A1 | 10/2006 | Wasicek et al. |
| 2007/0060911 A1 | 3/2007 | Webster et al. |
| 2007/0219619 A1* | 9/2007 | Dieck ............ A61F 2/07 623/1.13 |
| 2008/0172122 A1 | 7/2008 | Mayberry et al. |
| 2009/0192584 A1 | 7/2009 | Gerdts |
| 2013/0336752 A1 | 12/2013 | Crawford et al. |
| 2014/0277397 A1 | 9/2014 | Lorenzo |
| 2014/0288631 A1 | 9/2014 | Falotico et al. |
| 2017/0239046 A1 | 8/2017 | Essinger et al. |
| 2018/0236205 A1* | 8/2018 | Krautkremer ........... A61F 2/962 |
| 2018/0289884 A1 | 10/2018 | Criado et al. |
| 2020/0253766 A1 | 8/2020 | Walzman |

* cited by examiner

ORIENTABLE INTRACRANIAL OCCLUSION DEVICE AND METHOD

CROSS-REFERENCE(S)

This application claims the benefit of, and priority to provisional serial No. 62/921,378 filed Jun. 12, 2019, of which the entire contents of is hereby incorporated by reference.

TECHNICAL FIELD

The present disclosure relates to medical devices used to treat aneurysms and fistulas within unhealthy blood vessels, and, more particularly, relates to endovascular devices, including flow-diverting, covered, caped, fenestrated, branched, and other variable-porosity stents for use in intracranial or other, tortuous vasculature.

BACKGROUND

The prior art teaches the use of a number of devices to treat aneurysms. One such device is a differentially porous stent, having asymmetrical braiding or coils, so as to create areas of lesser or greater blood flow as may be desired. Fenestrated and branched devices have been effectively employed in the aorta and its immediate branches, and other applications having larger blood vessels with little tortuosity. Although the prior art has disclosed the theoretical application of such devices intracranially and in other tortuous and distal vasculature, no device or method has been described that can reliably deploy such devices in their desired radial orientations. The constraints of intracranial or other tortuous vasculature have to date precluded the use thereof in these areas. U.S. Pat. No. 9,775,730 B (Walzman) teaches a covered stent device capable of safe and effective delivery and deployment into tortuous vessels to effectively divert blood flow away from an aneurysm, fistula, or ruptured vessel while allowing blood to flow to healthy tissue distal to the targeted treatment area and still resulting in blood stasis and thrombus formation inside the aneurysm or fistula.

U.S. Pat. Publ. No. 2019/0151072 A1 (Walzman) teaches a caped stent providing a cover having a single attachment point and a free end that can be overlapped, thereby providing better conformity to target vessels than existing covered stents.

U.S. Pat. No. 8,398,701 B2 (Berez et al.) teaches a vascular occluding device deployable on a microcatheter. The occluding device includes an asymmetrical braid or differential lattice densities, as well as and corresponding/opposite variable densities of porosity to modify blood flow in a vessel while maintaining flow to surrounding tissue. Berez teaches that the flexibility of the device particularly suits it for treating aneurysms in the brain. Berez describes an embodiment including less coverage on one side at the same segment along the length of the cylinder versus the other side. For example, the area having less porosity (i.e., more coverage) should be positioned to cover an aneurysm for stagnation of flow in the aneurysm and subsequent thrombosis. The other side of the device having more porosity should be positioned on one side of a vessel or covering a branch to allow continuation of adequate flow and to prevent obstruction of flow to the branch and its distal tissue. However, Berez and other prior art devices have not devised a way to consistently and reliably deploy such devices in the optimal desired radial orientation, and no such devices are available.

An endovascular device may provide additional porosity by including a fenestration, allowing no obstruction whatsoever of blood flow to the origin of a branch vessel. This may be combined with a full cover at or near an opposing side to cut blood flow to a target aneurysm or fistula altogether.

A common blood vessel difficulty is the persistent blood flow in the aneurysm sac extrinsic to an endograft. In fact, this is the most common complication after endovascular aneurysm repair (EVAR) with stent grafts. Such endoleaks are ameliorated by a number of means. For example, Walzman's utility Application Ser. Nos. 15/732,147 and 15/732,365 teach the use of hydrogel to prevent endoleaks.

The prior art also teaches endovascular coiling as a minimally invasive technique performed to prevent blood from flowing into some saccular aneurysms. This treatment results in the coil inducing embolization (clotting) of the aneurysm, which prevents blood from flowing into the aneurysm, which in turn, prevents rupture and subsequent subarachnoid hemorrhage. Endovascular coiling however may result in procedural complications include thromboembolism, cerebral embolization, aneurysm perforation, parent artery occlusion, coil migration, arterial dissection, and others. The prior art also teaches stent-assisted coiling. The stent-assisted coiling also has some of the same short comings related to stent placement. For example, placing a stent in the parent artery requires prolonged use of antiplatelet agents to reduce the risk of thrombosis-based stenosis within the stent.

Some aneurysms and fistulas are ideally treated with covered stents, which can most directly cover the hole of the fistula or the neck of the aneurysm and reconstruct the vessel wall, immediately redirecting blood flow into the normal path of the parent vessel. However, there is no covered neuro-stent currently available in the United States. The U.S. Food and Drug Administration (FDA) has examined and tested such covered neuro-stents but none has "FDA approval," which means that the FDA has not decided the benefits over the existing treatment options outweigh the potential risks for the item's planned use. Additionally, there are currently no covered stents that are effective in severely tortuous anatomy in other parts of the body, including but not limited to splenic artery aneurysms and pulmonary arteriovenous fistulas.

A potentially significant use of covered neuro-stents is for the treatment of fistulas, particularly for Carotid cavernous fistula (CCF) which is an abnormal communication between the cavernous sinus and the carotid arterial system.

Other treatment of aneurysms includes surgical clipping of an intracranial aneurysm, which involves the application of a clip across the neck of the aneurysm. This treatment has several shortcomings including that it requires an open operation and physical manipulation of the brain. Sometimes surgical bypass is considered as well, but typically is associated with even higher rates of morbidity and mortality.

Additionally, the prior art teaches the use of flow diversion devices to divert flow away from the aneurysm by placing a mesh stent or a structure similar to a stent, on the aneurysm neck along the parent artery. The use of these devices allows for thrombus formation inside the aneurysm. However, increased technical complications can develop following the deployment of flow diverters.

Additionally, because flow diversion devices do not completely block flow, they are not effective in the treatment of fistulas and ruptured vessel. Similarly, there is currently no effective vessel-sparing treatment of an iatrogenic rupture of an intracranial artery. Current treatment requires closing the ruptured artery with coils and/or liquid embolics to stop the bleeding, usually with significant resulting morbidity from ischemic injury to that arterial territory. Furthermore, when treating aneurysms with these devices, the aneurysm thromboses over time, a lag period, and is not immediately cured. This leaves the patient at risk of aneurysmal rupture during the lag period. This can be especially problematic when treating ruptured aneurysms, which have high short-term re-rupture rates. Still further, when using current flow-diverting stents, many branch vessels are often crossed with the device, often resulting in narrowing's developing at the origins of these branches and sometimes resulting in occlusions and/or injury as well.

A need exists for an endovascular device capable of endovascular intervention for immediate cure of select intravascular aneurysm or fistula, while ameliorating the difficulties and shortcomings associated with the currently available technologies. More particularly, a need exists for a covered stent which allows freedom of motion and bending of the stent without kinking around tight bends in tortuous anatomy.

Most covered stents involve producing a cylinder of a stent "skeleton" or "frame" out of semirigid materials such as metal alloys, and then attaching an impermeable "cover" to the frame. The prior art teaches such attachments are diffuse and located throughout the covering of a stent, along fixed intervals of the covering and frame, and consequently significantly limit flexibility of the device.

All currently available flow-diverting stents have relatively uniform patterns of coverage and porosity throughout. No reliable means has been developed to successfully deploy a device that has differential porosity along different circumferentially radial segments.

For neuro-endovascular procedures (and other tortuous vascular anatomies), there is no known device or method which allows for precise positioning of such a differentially porous device to achieve an ideal ratio of covering and porosity where desired, and allowing flow where desired. Unlike larger vasculature (e.g., aortic) devices deployed through intracranial or other tortuous, circulatory anatomy are not susceptible to manual rotation at the hub end having an effect to rotate the intracranial end.

Thus, there is a need for a device that can be reproducibly positioned/landed in the appropriate orientation, such that an area of dense coverage and corresponding low porosity (or complete impermeability in an extreme case, or a fenestration in another extreme case) is deployed on the desired side, while low density coverage and corresponding high porosity (and/or fenestration with no coverage at all in an extreme case) is deployed on the desired side. Additionally, there is a need for branched covered and flow diverting devices in distal and tortuous vasculatures. Currently such devices are not available for use in neuro-endovascular procedures, and are similarly not available in other tortuous vascular anatomies, because devices, systems, and methods to deploy such devices consistently and accurately in the desired orientation do not exist.

Similarly, in cardiac, peripheral and other vasculatures there is a need for more effective bifurcated stent constructs, to minimize the obstruction of side branches during various stenting procedures. The current system allows accurate positioning of fenestrations in a multiple stent construct, to minimize the risk of obstructing branches while more effectively placing stents across bifurcations. These constructs can effectively treat atherosclerotic narrowings, aneurysmal diseases, dissections, fistulas, and other pathologies.

Therefore, were one to deploy such a device, the ultimate orientation upon positioning would be random. For example, with the case just described, the exact opposite from ideal could occur. That is, the fenestration might end up over the aneurysm, thereby increasing flow to the lesion; while the area of high-density coverage might end up over the origin of a normal branch vessel, causing a lack of flow to the branch, and subsequent ischemic injury. The device can work easily in straight anatomy of short distances, where a catheter can easily and accurately be rotated along its entire length from its proximal hub.

Again, using the extreme example of a fenestrated device, branched devices could also be built in vivo, by deploying a fenestrated device with the fenestration over the origin of a branch, and the deploying another device from the fenestration, and into the branch. The second device can be slightly larger in diameter proximally, at the fenestration, to ensure slight overlap, without covering the primary distal branch/vessel. Similarly, a device could be built that includes multiple branches, through multiple fenestrations, provided all fenestrations are in proper relative distance and orientation to the native branches.

This concept was described by Ruiz in U.S. Pat. No. 6,261,273 B1 for an Access System for Branched Vessels and Methods of Use. However, Ruiz discloses the building of a directional sheath or catheter in vivo, rather than an implant. Like the Berez device, however, the Ruiz device can work easily in straight anatomy of short distances, where a catheter can easily and accurately be rotated along its entire length from its proximal hub.

Rotation is not effective for positioning in tortuous and/or longer vascular anatomies, in which catheters do not respond in a similarly predictable fashion. This presents a difficulty when a stent device, which is usually crimped for delivery, is advanced into a delivery catheter, typically using a delivery wire and/or hypotube, in a particular arrangement. The stent will exit the delivery catheter in an unpredictable arrangement or orientation.

Furthermore, "Y" shaped stents were not heretofore practical to deploy or assemble at branches in cranial or other tortuous vascular anatomy. There exists a need for Y-shaped, bifurcated, and otherwise branched stent devices that may be effectively deployed or assembled in such anatomy. Additionally, in order to safely and accurately deploy such devices, novel devices and methods are needed to more precisely land the proximal end of such stent devices.

Thus, a need exists for a covered or partially covered neuro stent capable of use intracranially or in other tortuous anatomy outside of the brain, which device's more porous and less porous areas may be positioned as desired with respect to one or more branch vessels and at least one aneurysm or fistula, respectively. Additionally, there is a need for similar covered or partially covered branched devices as well. The present invention satisfies these unmet needs.

A need also exists for fenestrated and variable coverage and variable porosity stents, wherein the fenestrations and regions of decreased porosity along the circumference of a device can be accurately positioned, in any anatomy. This can be used in vascular applications as well as both vascular and nonvascular endoscopic applications.

SUMMARY

Disclosed is a method and device to correctly orient an intracranial occlusion device, such as a stent having differential porosity, with respect to desired areas of greater or lesser blood flow (e.g., branch vessels and aneurysms, respectively). The present invention is particularly adapted for use in treating aneurysms and fistulas in intracranial or other tortuous vasculature, as well as vascular narrowing and other pathology.

The present invention may be used for treatments requiring a device be precisely oriented to other devices after delivery. The invention should be particularly helpful for the reorientation of devices which have traveled through long and twisted tubes prior to reaching the target area. The present invention may also be used for treatments requiring that the device be precisely oriented to other structures after delivery. For example, the present invention might be particularly useful for orienting asymmetric discs in aneurysm necks or stents in GI/biliary tract (i.e.—vascular, endoscopic, etc.).

There is difficulty in achieving such a desired orientation due to several factors. The lumen of delivery catheters (through which stents may be deployed) are typically round. Similarly, the outer diameter/surface of wires over which most balloon-mounted stents are delivered are round, as are the inner diameter surfaces of the delivery balloon catheters. As such, stents will generally rotate in the lumen during deployment in an unpredictable fashion.

Additionally, as catheters are advanced through tortuous anatomy, the catheters themselves can twist, and do so in unpredictable fashion. Achieving the desired radial placement, therefore, becomes a matter of chance, with a concomitant chance of achieving the opposite of the desired result, with negative consequences. The following devices and procedures are disclosed to overcome this difficulty.

Differentially porous stent or such braided-type, mesh type, or weave-type therapeutic devices may be oriented to a degree of desired flow or blockage. Some stents described by Walzman (Ser. No. 16/214,130—"caped stent") optionally having a free-floating cover. The floating cover is designed to optimize insertion into tortuous anatomy. Among its unique structural elements are a single circumferential attachment point at one end (as small as 1 nm), overlapping circumferential shingles and overlapping geometric shingles.

The disclosed device may optionally be deployed under flow arrest, via pharmacologic means, or via delivery through a balloon guide catheter with temporary balloon inflation or other means, to minimize the possibility of blood flow affecting positioning as it is unsheathed.

In still other embodiments, the coverings may not fully encircle a given segment of the frame, thus allowing some stents to be covered or have decreased porosity along a portion of its circumference while being uncovered or have increased porosity at a different circumferential side of the same segment. This can sometimes allow preservation of the origin of a branch vessel that might arise from the parent vessel along the same segment of the parent vessel's pathology for example, opposite to a fistula or the neck of an aneurysm. The present invention further discloses devices and methods to more accurately position the proximal end of a stent, so if a fenestration in a first stent is placed over the origin of a branch, a second stent can be accurately landed to overlap the first stent around the fenestration, so as to avoid leaks between the two stents while also avoiding unwanted obstruction of the primary vessel by the proximal end of the second stent.

More accurate "landing" of a proximal end of a stent can be achieved with the unique devices and methods described herein. The present disclosure describes an inner "unsheathing" hypo-tube or wire, which at its distal end can have reverse cone "wings" that can come back and over a stent. The stent can be mounted on the distal end of an outer hypo-tube. The inner hypo-tube goes through the outer hypo-tube, with its wings extending back over the distal end of the outer hypo-tube, and over the stent mounted thereon, to constrain the stent, which is often self-expanding in this variant. Once the stent is in the desired position, the outer hypo-tube can be held in place, while the inner hypo-tube is advanced. As the inner hypo-tube is advanced, its back wings are also advanced, and releases its constraint from the stent in a proximal to distal fashion. Thereby, the proximal stent is released from its constraint first, and expands for deployment. If the proximal portion position of landing is not optimal, it can be re-sheathed by pulling the inner hypo-tube back again. The stent can then be repositioned and deployment can resume.

The current invention utilizes catheters and wires with non-round shapes which fit snugly on top of each other. Depending on the device, sometimes the catheter may be deployed first, and a stent may be delivered therethrough over a corresponding shaped wire; wherein the wire shape correlates with the inner diameter of the stent delivery catheter. In some configurations, the wire is delivered first to the lesion site, and a stent mounted catheter is then delivered over it; these can all be "rapid-exchange" or "over-the-wire" delivery systems; in other configurations a catheter with a particular non-round inner diameter circumferential shape can first be delivered to a lesion site over any wire, the initial wire is then removed and then a stent mounted on a corresponding-shaped outer-diameter wire is delivered through the catheter and to the lesion site. Although not exclusively, the former configuration is more common with balloon-mounted stents, and the latter configuration is more common with self-expanding stents.

It is critical that all wire-catheter combinations are snug enough that the wire cannot rotate relative to the catheter, even if there is a stent between the two over a portion of the wire, while still having enough freedom of movement to allow delivery of the catheter over the wire, or the wire through the catheter, without undo force.

In some versions for branched stenting, a wire can be placed in both branches first, where one branch's wire can be placed through the distal end hole of the delivery catheter, while the catheter can have a side hole at the site of a stent side fenestration, and the second branch's wire can be backloaded into the side hole, which may help position the side hole appropriately at the origin of the side branch, while also keeping wire access to the side branch.

In other versions for branch stents, the initial positioning of the initial wire or catheter can dictate the way the subsequent stent or wire is delivered, respectively, based on documentation of degree of rotation from the back of the wire or the hub of the catheter using "12 o'clock markers," adjacent the wire or hub and at the lesion site. In these versions, some stents can also have a dual lumen delivery catheter, wherein the primary lumen extends from the distal end hole, but the secondary lumen ends at a side hole at the site of a stent fenestration. Thus, a stent can be positioned across a lesion in one branch in the appropriate orientation relative to a crossed side branch. Then a second wire can be delivered into the side-hole ending lumen, through the side hole, and into the side branch, before the first stent is deployed. Then, after the first stent is deployed, the stent-delivery catheter can be withdrawn, while leaving at least the side branch wire in place. A second stent can then be delivered over an independent stent delivery catheter into the side branch, and deployed either in the side branch only, or if desired in the side branch and extending into the primary branch, overlapping the proximal portion of the first stent.

Once the initial geometric non-round wire or geometric non-round inner lumen catheter is positioned optimally, imaging can be used to confirm the orientation of the tip of the corresponding wire or catheter relative to its hub. The hub can have a "12 o'clock" marker, and the tip can have a corresponding radiopaque marker. Subsequent imaging with x-ray, 3d x-rays, CT imaging, echocardiography, ultrasound, IVUS, or other modalities can then confirm the relative rotation of the tip near the target lesion relative to the hub. Any inner wire mounted stent system or outer catheter mounted stent system can then be rotated a corresponding amount before being loaded into the proximal hub of the catheter or onto the proximal wire, respectively, to account for the recorded degree of rotation of the already delivered catheter or wire, respectively, to ensure subsequent accurate orientation of delivery and deployment. Fundamentally, in somewhat tortuous anatomy most catheters, wires, and stents cannot be accurately rotated at the target site from the proximal hub. However, the current invention relies on a fixed degree of random rotation during initial delivery of the initial wire or catheter to be recorded accurately and subsequently accounted for, allowing accurate orientation of device delivery and placement. In some cases, trial retrievable stent devices or similar devices can also be used to determine or confirm the orientation of the wire or catheter at the lesion site.

Figure 1A:
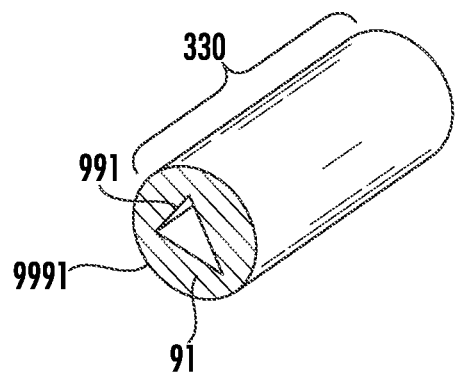
FIG. 1A shows a perspective view of a cylindrical delivery catheter 330 having a triangularly shaped lumen 991 that correlates with the inner lumen cross-sectional shape of the catheter. In the system, in terms of the intersection of the wire between the catheter delivering the stent-in some systems the stent can be loaded on a wire and delivered on the wire, within a pre-positioned catheter. In other embodiments, the wire will be delivered first, and the stent will be delivered mounted on a corresponding catheter, often on the outside of a balloon mounted on the catheter. The key to proper device positioning is that the wire and stent system, or the catheter and stent system, must be snug enough so that the catheter and wire cannot rotate relative to each other, but will maintain a constant circumferential orientation relative to each other; while they must also have sufficient spacing relative to each other to allow one to slide over the other without undo difficulty.

FIG. 1A shows an embodiment of delivery catheter 330 with a generally rounded cross-sectional outer diameter shape 91 with a non-round inner lumen 991, in this particular case being triangular. It also shows a proximal end 9991 of said delivery catheter.

Figure 1B:
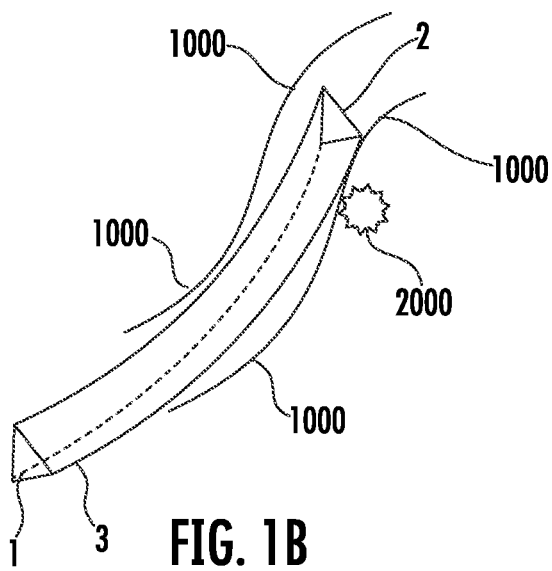

FIG. 1B shows an embodiment of delivery catheter lumen 3 without its cylindrical sheathing (not shown), having a proximal end 1 and a distal end 2, where the proximal end 1 is in the same geometric plane as delivery catheter proximal end 9991 and has been passed through vessel 1000 such that distal end hole 2 is proximal to target aneurysm 2000.

Figure 1C:
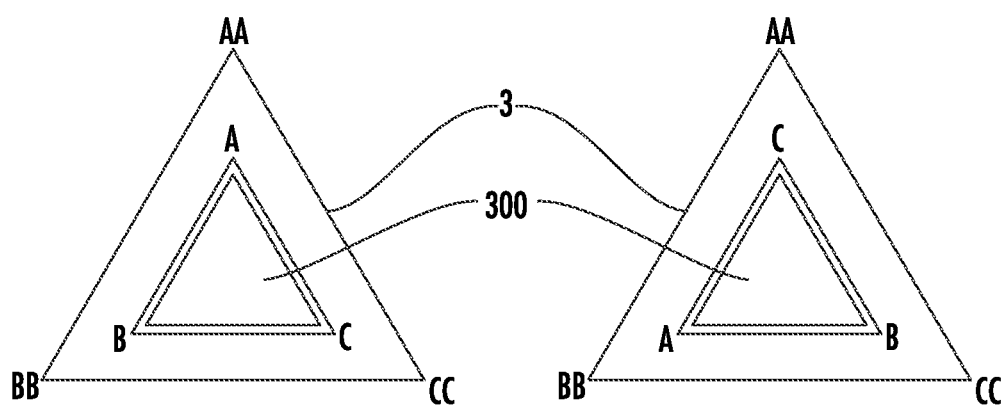

FIG. 1C is a cutaway view of delivery catheter lumen 3 having a triangular lumen with vertexes AA, BB and CC and with interior A-B-C angles, and pusher wire 300 passing therethrough. For the purposes of nomenclature, if the triangular lumen has its top vertex labeled A is rotated counter clock-wise 120°, then the A vertex will be located on the lower left side of the triangular lumen. The left side of FIG. 1C shows the initial relative orientation of the vertexes AA, BB and CC and with interior A-B-C angles, and pusher wire 300 passing therethrough. The right side of FIG. 1C shows the same lumen 3 and the same pusher wire 300 with a counter clockwise 120° relative orientation of the vertexes AA, BB and CC and with interior A-B-C angles, and pusher wire 300 passing therethrough but at offset C-A-B angles, in order to deliver a differentially porous occlusion device (not shown) at a 120° counter clockwise relative orientation. In short, the delivery catheter upon delivery to a target vessel location has a fixed relative position to the target vessel location. A pusher wire communicates with the delivery catheter so as to allow the delivery of an item (such as a porous occlusion device) to the target vessel location at the same fixed orientation as the delivery catheter, accounting for rotation of the delivery catheter between the proximal hub outside the patient's body and the distal end of the delivery catheter after random rotations during delivery through tortuous anatomy. Thus, if the distal end is visualized as being in a desired orientation if the occlusion device or other device was delivered in the 12 o'clock position, then the occlusion device can be introduced from the packaging catheter into the delivery catheter with no rotation when the distal end of the packaging catheter is introduced into the proximal hub of the delivery catheter. However, if the 12 o'clock marker is recorded as being rotated relative to the target lesion, then the degree of rotation can be recorded, and a corresponding degree of rotation of the packaging catheter will rotate the occlusion device into the desired position upon delivery through the delivery catheter to the target lesion. As shown in FIG. 1C, the porous occlusion device is delivered to the target vessel location at an orientation which counter clockwise 120° relative orientation of the vertexes AA, BB and CC of the delivery catheter.

Figure 2:
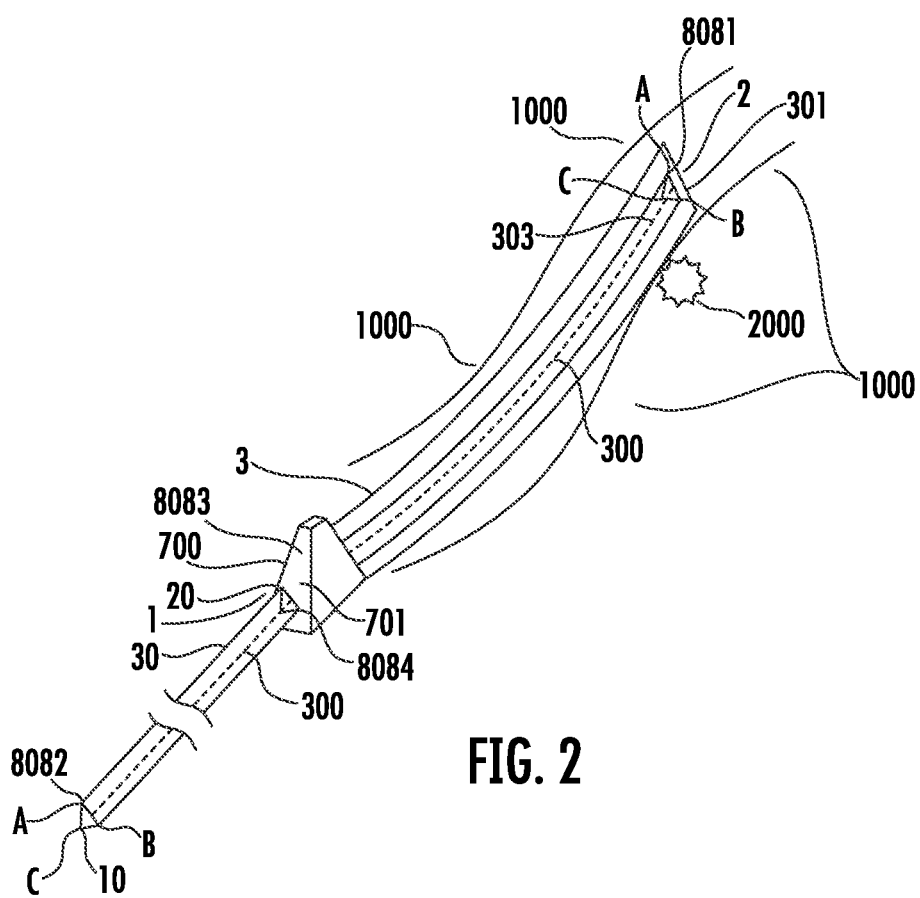

FIG. 2 shows proximal end 10 and distal end 20 of stent-packaging catheter 30 (outside patient's body), hub 700 (which is outside patient's body) attached to delivery catheter lumen 3, packaging-catheter hub port 701 displaying push-wire 300 running therethrough, and further showing push-wire 300 (in dashed lines extending through delivery catheter lumen 3) continuing through delivery catheter lumen 3. The push-wire 300 has its distal end 303 releasably attached to stent 301 (please note that 301 runs complete through the delivery catheter with the stent preloaded and crimped onto the triangular outer surface of said wire, in one preferred embodiment) proximal to target aneurysm 2000. The distal end 20 of stent-packaging catheter 30 is disposed inside hub port 701. The delivery catheter lumen 3 is oriented with triangular proximal end hole inside hub port 701, and aligned with substantially similarly shaped distal end 20 of stent-packaging catheter 30 in FIG. 2, and triangular distal end hole 2 proximal to target aneurysm 2000). Delivery catheter lumen 3 is deployed within vessel walls 1000.

Figure 3:
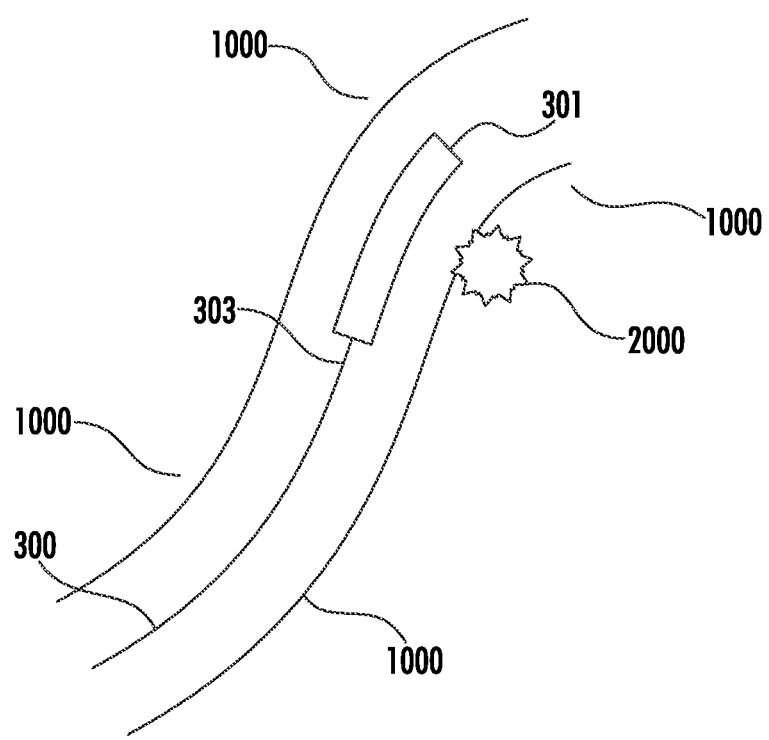

FIG. 3 shows push-wire 300 and stent 301. It should be noted that the wire in most embodiments should continue beyond the stent slightly; although it doesn't have to, but the wire should at least continue until the distal end of the stent, i.e., within the stent. The push wire distal side 303 is not the distal end of the wire-it is on the distal side, but not an end in most embodiments and is disposed within vessel walls 1000 following removal of delivery catheter lumen 3 (shown in FIG. 2).

Figure 4:
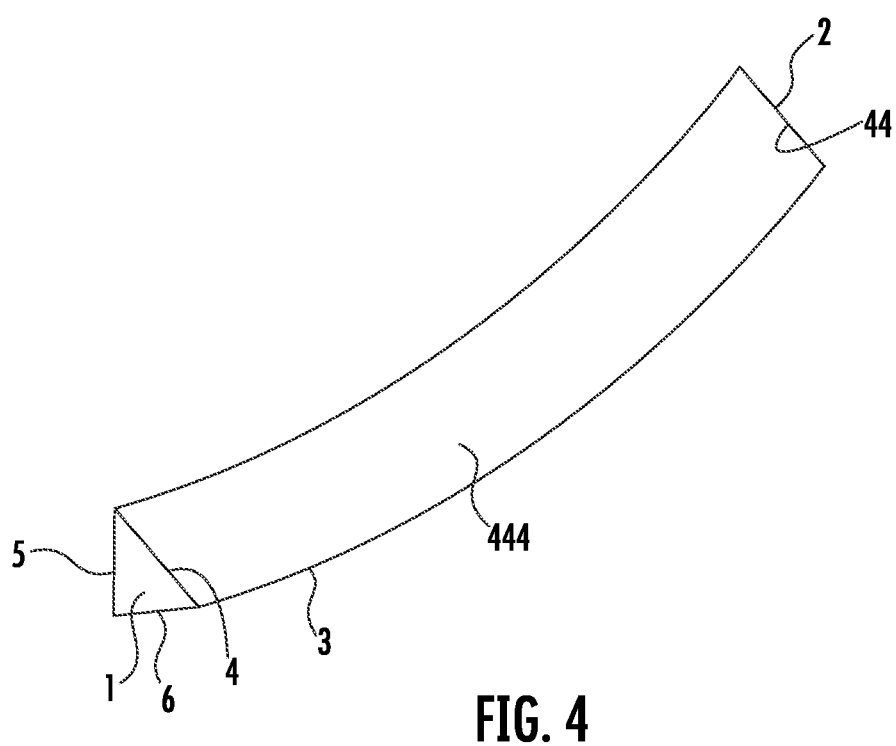
Figure 5:
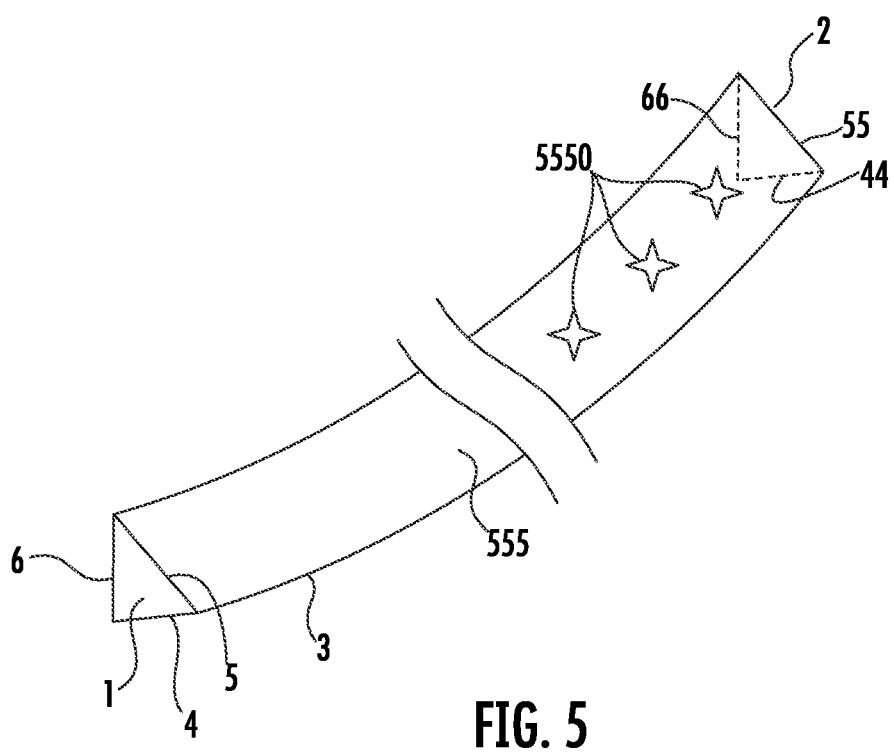

FIG. 4 shows an interior view of delivery catheter lumen 3 having a triangular shape, composed of proximal sides 4, 5 and 6, corresponding with distal sides 44 (oblique distal sides 55 and 66 behind 44 are shown in FIG. 5); facing side 444 illustrates the full length of the catheter side beginning at proximal side 4 and ending in distal side 44. Alternative embodiments (not shown) may employ other regular non-round shapes such as rectangles, pentagons, squares, ovals, ellipse, stars and others.

FIG. 5 shows an adjacent face 555 of the interior of delivery catheter of FIG. 4 (or FIG. 4 rotated once 120 degrees clockwise). Face 555 begins at proximal side 5 and ends in distal side 55 (oblique distal sides 44 and 66 behind 55 shown in dashed cutaway). Face 555 further includes radio-opaque orientation-aid markers 5550. It important to note that the use of triangular stents while possible, may not be the preferred embodiment because most vessels have circular cross sections. The two preferred embodiments are: 1. A catheter with the "triangular" inner lumen is advanced first to the lesion, and then a stent preloaded on a "triangular" wire is advanced through that catheter; and 2. A "triangular" shaped wire is advanced to the lesion, and then a stent loaded on a catheter with a "triangular" inner lumen (most often on a balloon on the catheter) is advanced over the wire. In either scenario, a cylindrical stent has to be preloaded and pre-crimped down onto either the wire (in the former scenario) or onto the balloon on the catheter (in the latter scenario). Most often this loading and crimping is done during the manufacturing and packaging, and the physician receives the device preloaded. Only in the rarest of scenarios is a wire advanced through a triangular stent as describe above.

Figure 6:
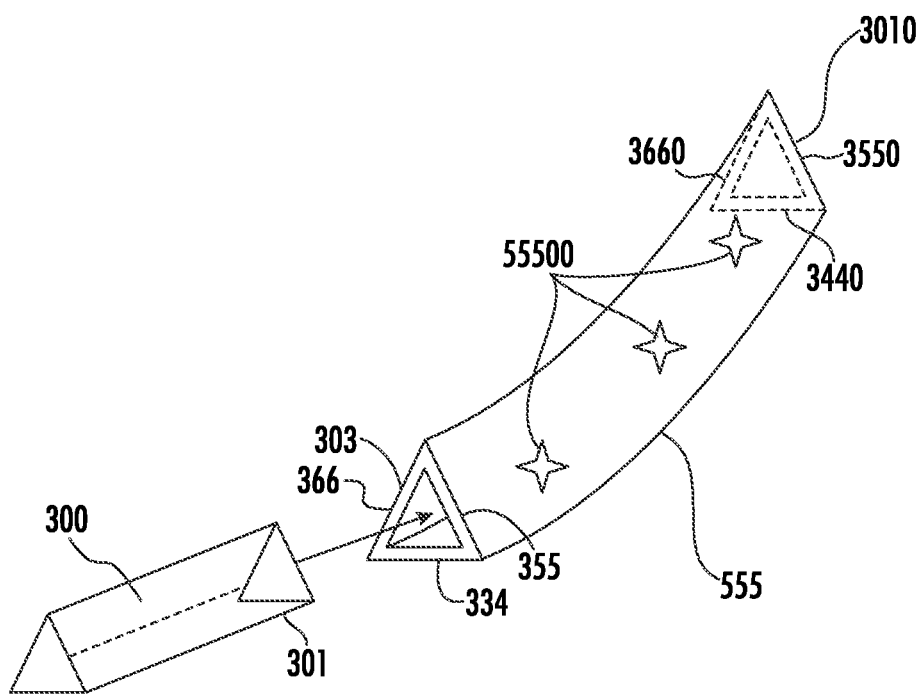

FIG. 6 shows a stent 301 without its cylindrical sheathing (not shown) loaded on push-wire 300 with an arrow showing the entry of the push wire 300 (wherein the push-wire 300 is triangular) into proximal end 303 of delivery lumen 555 and distal end of delivery lumen 3010. The delivery lumen 555 has an internal lumen which is shaped into a structure to allow the entry and passage therethrough of the triangular shaped push-wire 300, and with the stent 301 crimped into a triangular shape thereupon, with distal end 3010 of the delivery lumen 555 and triangular edges on a plane with delivery lumen 303, namely edges 334, 355 and 366. Triangular edge 355 forms a planar length terminating in edge 3550 in this substantially unrotated example. On the plane, resides radio-opaque markers 55500. There may be multiple radiopaque markers to aid in confirming the position of the distal catheter. In a preferred embodiment there is a distinct 12 o'clock marker at the distal end as well, and a 12 o'clock marker at the proximal hub outside the patient's body that can be directly visualized. It should be noted that the stent needs to be mounted on a wire or a catheter-in this case a wire-so the wire will extend at least to the distal end of the stent in most embodiments, and usually slightly beyond/longer.

Figure 7A:
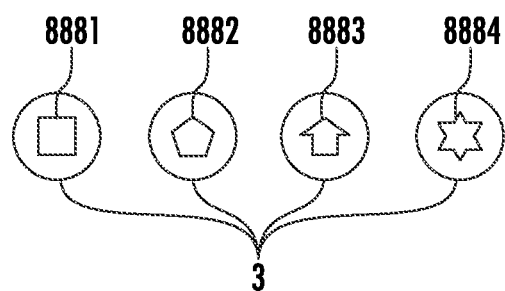

FIG. 7A shows delivery catheter lumen 3 may have square 8881, pentagon 8882, arrow 8883 or star 8884 shaped interior lumens. The interior lumen may be virtually any shape that is not round.

Figure 7B:
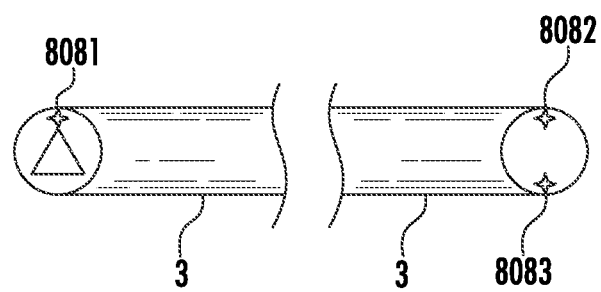

FIG. 7B shows delivery catheter lumen 3 which has a triangle shaped inner lumen and a marker 8081 at the 12 o'clock position on the distal end, and a radio opaque marker 8082 at the 12 o'clock position on the proximal end and in this example a different radio-opaque marker 8083 at the 6 o'clock position at the distal end.

Figure 8:
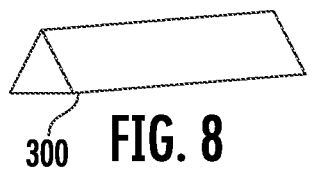

FIG. 8 shows pusher wire 300.

Figure 9:
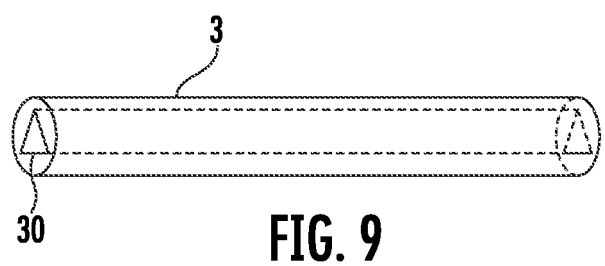

FIG. 9 shows packing catheter 3 with triangular inner-lumen 30 (dashed-line).

Figure 10:
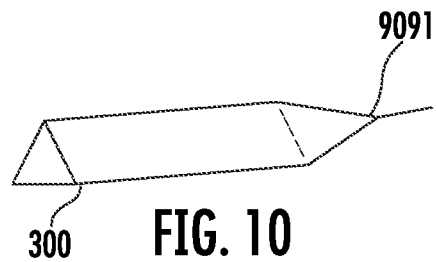

FIG. 10 shows an embodiment wherein distal end of pusher wire 300 is tapered 9091.

It should be noted that FIG. 10 is a non-limiting embodiments of pusher wire 300 may have rounded, pointed, or other tips at the distal end.

Figure 11:
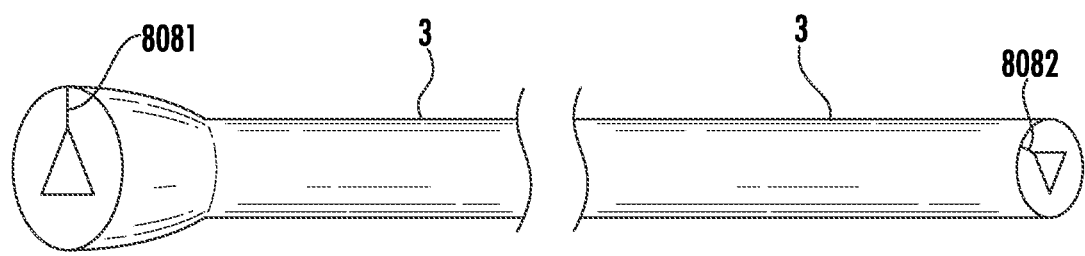

FIG. 11 shows a twisted catheter where in delivery catheter 3 which has a triangle shaped inner lumen, a marker at the 12 o'clock position on the proximal end hub 8081 and a corresponding 12 o'clock radio opaque marker on the distal end 8082 that has rotated to the 10 o'clock position.

Figure 12:
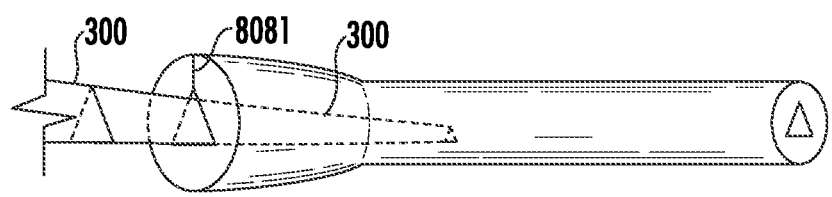

FIG. 12 shows delivery catheter lumen 3 with a pusher wire 300 and a marker at the 12 o'clock position on the proximal end hub 8081.

Figure 13:
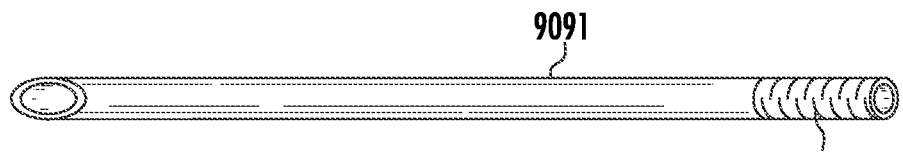

FIG. 13 shows reverse un-sheathing stent, more particularly, a stent 9090 loaded on an outer pusher hypo-tube 9091. It should be noted that the outer pusher hypo-tube 9091 may be round as show only if rotation is not required. If rotation is required, then a non-rounded surface is preferred.

Figure 14:

FIG. 14 shows an inner un-sheathing hypo-tube 9092 with wings 9093 and a wire lumen 9094. The wings 9093 extend back and cover stent 9090 mounted on the outer pusher sheath/outer hypo-tube 9091. It should be noted the unsheathing hypo-tube is inside the outer hypo-tube, except the wings 9093 which are outside both the inner hypo-tube and the stent 9090.

Both the inner hypo-tube 9092 and outer hypo-tube 9091 can optionally have an "over-the-wire" configuration and/or a rapid exchange configuration. Thus, by advancing inner hypo-tube 9092 and holding the outer hypo-tube 9091 still the covered stent 9090 is unsheathed, proximal end first.

Figure 15:
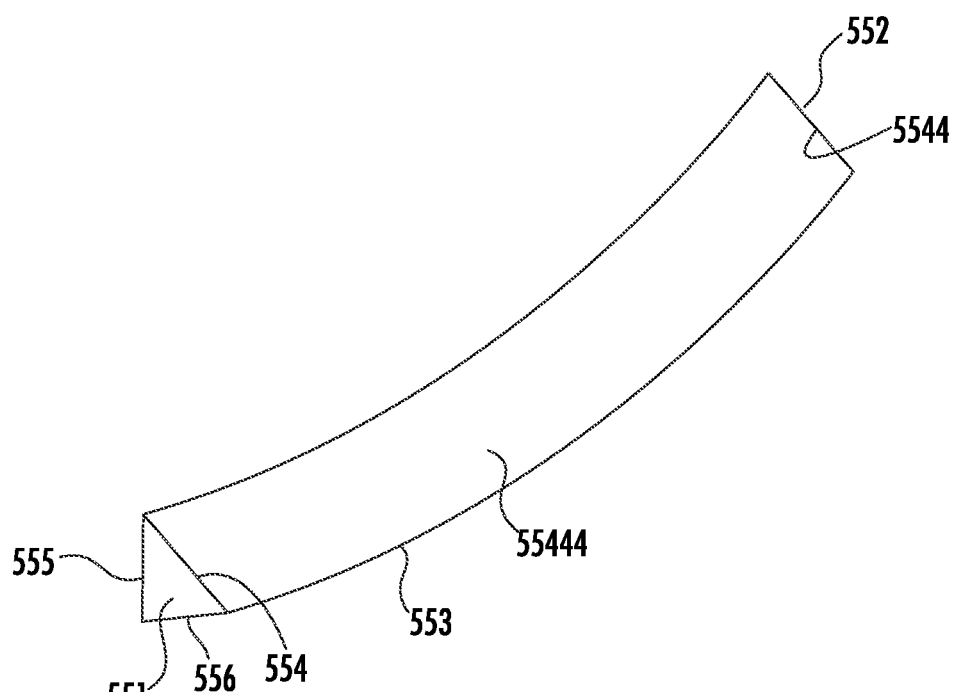

FIG. 15 shows a wire 553, more specifically, an exterior view of delivery wire having a triangular shape, composed of proximal end side designated as 554, 555 and 556, with each corresponding to a side and a distal end (for example 554 proximal end side, corresponds with 55444 facing side and 5544 distal end side). FIG. 15 shows facing side 55444 and the full length of the wire side beginning at proximal side 554 and ending in distal side 5544, shown in this example without significant rotation between the proximal end and the distal end of the wire. Alternative embodiments (not shown) may employ other non-circular shapes such as rectangles, pentagons, squares, ovals stars and others. 551 is the proximal end of wire and 552 is the distal end of wire.

DETAILED DESCRIPTION

The embodiments of the device and variants of the device of the present invention are set forth with reference to the above drawings.

Referring to FIG. 1A, a perspective view is shown of a cylindrical delivery catheter 330 having a triangularly shaped lumen 1. The present invention discloses a traditional cylindrical delivery catheter with a linear lumen such as a triangle, square, other rectangle, star, hexagon or so on. Alternatively, it may have a pronounced non-round shape such as an oval or ellipse. The linear lumen is designed to allow the delivery of a push wire which has a similar shape, adapted to be inserted into the lumen 1 at differing, fixed relative positions.

Now referring to FIG. 1B, shown is an embodiment of delivery catheter lumen 3 without its cylindrical sheathing (not shown). The delivery catheter lumen 3 has a proximal end 1 and a distal end 2, and has been passed through vessel 1000 such that distal end hole 2 is proximal to target aneurysm 2000. Delivery catheter lumen 3 is inserted into blood vessel 1000 until stopped such that distal end 2 is proximal to target aneurysm 2000. Due to the linear geometry of the lumen 1, the delivery catheter lumen 3 has a set orientation with respect to having one side closest to the target aneurysm 2000.

Now referring to FIG. 1C, shown is a cutaway view of delivery catheter lumen 3 having a triangular lumen with A-B-C angles, and pusher wire 300 passing therethrough at offset C-A-B angles, in order to deliver a differentially porous occlusion device (not shown) or a fenestrated device at a 240 degree clockwise rotation angle to deploy at a desired orientation. A similar setup may be used to deliver other devices, such as aneurysm neck caps which may have an asymmetric shape to cover an asymmetric aneurysm neck, previously described by Walzman (U.S. Pat. No. 10,543,015), and other devices, in their desired optimal orientation. When any occlusion device is used, supplemental additional occlusion devices may optionally be used as well. The present invention teaches that the orientation of a push-wire may be fixed outside the patient's body by fixing its relative orientation with respect to the delivery catheter lumen 3. The delivery catheter lumen 3's orientation with respect to target aneurysm 2000, having been established prior to insertion of push-wire 300 via imaging, allows the user of the device of the present invention to properly insert the push-wire 300 to achieve proper orientation with respect to aneurysm 2000 without turning the push-wire 300 inside the patient.

Now referring to FIG. 2, shown is proximal end 10 and distal end 20 of stent-packaging catheter 30 (outside patient's body), hub 700 (outside patient body) attached to delivery catheter lumen 3, packaging-catheter hub port 701 displaying push-wire 300 running therethrough. Also shown is push-wire 300 (in dashed lines extending through delivery catheter lumen 3 and continuing through delivery catheter lumen 3). The push-wire 300 has its distal end 303 releasably attached to stent. (Note: 301 is drawn to show the stent is located at the distal end of delivery lumen. The stent is not shown in FIG. 2 because it is covered by another structure of the present invention) proximal to target aneurysm 2000. The distal end 20 of stent-packaging catheter 30 is disposed inside hub port 701, delivery catheter lumen 3 (oriented—see A, B, and C triangle tip designations) with triangular proximal end hole inside hub port 701 and triangular distal end hole 2 proximal to target aneurysm 2000. The delivery catheter lumen 3 is deployed within vessel walls 1000. Additionally, the present invention discloses a single "12 o clock" marker 8083 on the hub 700, and a single radio-opaque "12 o'clock" marker 8081 on the distal catheter tip. More specifically, FIG. 2 shows delivery catheter lumen 3 which has a triangle shaped inner lumen and a radio opaque marker 8081 at the 12 o'clock position on the distal end, and a marker 8082 at the 12 o'clock position on the proximal end of the hub 701 of the delivery catheter. Additionally, the packaging catheter also needs a marker, but only at its distal end, shown as 8084.

Packaging catheter 30, which has a corresponding 12 o'clock marker at its distal end 20, is joined by the practitioner to hub 700 at port 701 with its 12 o'clock marker 8083 such that stent 301 and push-wire 300 are oriented as desired so as to present the minimally porous surface of the stent 301 substantially toward the target aneurysm 2000, when the current invention of a matching non-round wire and inner catheter lumen is used for delivering a differentially porous flow-diverting stent device. In one scenario, the least porous stent section may be completely impermeable to fluid and blood. In another scenario, the least porous section of a stent may have no struts at all, representing a fenestration or hole in said device.

Now referring to FIG. 3, shown is push-wire 300 and stent 301 disposed at distal push-wire 303 within vessel walls 1000 following removal of delivery catheter lumen 3 (shown in FIG. 2). Once stent 301 is proximally placed next to aneurysm 2000, the tent 301 is activated or released from its external constraints and expands such that the substantially nonporous side of the stent 301 abuts the aneurysm 2000, while the other sides of a cylindrically elongated stent 301 are porous to promote blood flow to any side branches it may cross. The stent is usually always a cylinder when expanded-it can just be temporarily crimped into an alternate shape when loaded on a wire, catheter, or balloon-when loaded on a balloon the balloon will usually be round/cylinder as well, but the catheter or wire it is loaded on needs to be the proper shape, both proximally and usually distally to the stent as well, and most often along the balloon segment, so the stent takes the proper course and remains in the proper orientation. Thus, in some iterations the deflated balloon is also crimped down onto a continuously proper shaped catheter, to assume this shape until inflation as well. When being crimped on a round balloon in this scenario, the balloon is collapsed and deflated and mounted on a catheter of an appropriate shape, so the deflated balloon and the non-expanded shape get crimped down in the same shape (if necessary an external crimper of the same shape can sometimes be used in the crimping process as well). But when the balloon is inflated and/or the stent is expanded the balloon and/or the stent will form a cylinder shape in most embodiments.

Now referring to FIG. 4, shown is an interior view of delivery catheter lumen 3 having a triangular shape, composed of proximal sides 4, 5 and 6, corresponding with distal sides 44 (oblique distal sides 55 and 66 behind 44 are shown in FIG. 5); facing side 444 illustrates the full length of the catheter side beginning at proximal side 4 and ending in distal side 44. In this example there is no significant rotation between the proximal side end and the distal side end.

The orientation of lumen of delivery catheter lumen 3 should be clearly identifiable. FIG. 4 shows a triangular shape having sides 4, 5 and 6 on the proximal end, 44 at the distal end of face 444. Alternative embodiments (not shown) may employ other defined non-round shapes such as rectangles or stars.

Now referring to FIG. 5, shown is an adjacent face 555 of the interior of delivery catheter of FIG. 4 (or FIG. 4 rotated once 120 degrees clockwise), face 555 beginning at proximal side 5 and ending in distal side 55 (oblique distal sides 44 and 66 behind 55 shown in dashed cutaway); facing side 555 further includes radio-opaque orientation-aid markers 5550. Some preferred embodiments may also have a 12 o'clock radio-opaque marker at the distal end for determining distal catheter rotational positioning relative to a lesion or a side branch or other structures. FIG. 5 is a rotated image of FIG. 4 displaying the opposing plane 555 which terminates at side end 5 on the proximal end, and 55 on the distal end. On surface or plane 555, radio-opaque markers 5550 allow the user to ascertain the relative orientation of one side of the delivery catheter lumen 3. Using this information, the packaging catheter 30 may be properly oriented in hub port 701 such that when push-wire 300 and stent 301 are proximal to aneurysm 2000, they are properly aligned and oriented in the desired configuration.

Now referring to FIG. 6, shown is a stent 301 (Note: 301 shows a location of the stent which is often covered by other present invention structures) attached to push-wire 300 at distal end of push-wire 300 and lined up with the proximal end of delivery lumen 5555. The stent 301 has a substantially cylinder shape when fully open and unconstrained, but is introduced cinched down on the triangular wire in a triangular in shape, with distal end of delivery lumen 555 and triangular edges on a plane with proximal end 303, namely edges 334, 355 and 366. At the distal end 3010 of delivery lumen 301, triangular edge 3550 is shown, and dotted lines disclose the other two triangular edges 3440 and 3660. Triangular edge 355 forms a planar length terminating in edge 3550, in this substantially nonrotated example. On the plane, resides radio-opaque markers 55500.

First Method.

Use a delivery catheter with a "12 o'clock" marker at the proximal hub of catheter and a fixed and continuous non-round inner-circumference luminal shape. The 12 o'clock marker may be disposed on the hub and on the delivery catheter tip (i.e., radio-opaque on the catheter tip). The user inserts the stent-packaging catheter having a differentially porous stent or occlusion device mounted on a push-wire therein. After testing to determine the degree of rotation between the hub and the tip, the user rotates the packaging catheter at the hub to the desired indicator so that said device will be oriented in the desired position when delivered to the target sight at the distal end of the delivery catheter.

The indicator may be disposed in any position on the hub to point to any direction on the hub, but terming this a 12 o'clock indicator or marker is convenient for describing positions relative to the marker for anyone familiar with an analog clock face. For example, instructing a user to rotate the hub to "3 o'clock", "6 o'clock", or "9 o'clock" intuitively suggests a quarter turn, half turn, and three-quarter turn, respectively, with other "times" referring to approximate positions between these 90-references (e.g., 2 o'clock, 5 o'clock or 11 o'clock). The same effect could be achieved by reference to a "North" marker, utilizing terminology such as East, South, and West (or interstitial positions such as ESE or NW), but "12 o'clock" is a preferred reference. The ability to rotate the relative orientation of the delivery catheter within a 360° range manually, not the terminology employed, is material.

Use a packaging catheter having a distal marker, advance a test stent or final stent or other directional device at a particular orientation relative to the 12 o'clock marker on the delivery catheter. The stent (or other marked endovascular device) will generally end in a substantially similar orientation. If introduced at the 12 o'clock position at the hub, it will typically deliver at whatever orientation the distal end 12 o'clock marker sits. If a different position for the device is preferred, it must be rotated a corresponding degree and direction relative to the end marker to be deployed in the desired configuration. Such rotation is achieved by rotating the delivery catheter in a desired amount and direction that the final device should be rotated relative to the end 12 o'clock marker, before introducing it into the delivery catheter, and introducing it into the delivery catheter in such orientation. It is clear that when using a triangular lumen and wire, the packaging catheter can only be rotated into only 3 circumferential positions relative to the delivery catheter. In order to accomplish additional rotational positioning choices, the stent or other device may be pre-loaded into the delivery packaging at varying degrees relative to the 12 o'clock marker. This would most often be done during packaging by the manufacturer, before delivery. The devices and/or their packaging would be appropriately labeled to identify the position of the device relative to the 12 o'clock marker on the distal end of the packaging catheter. The process may be repeated to verify that the markers on the delivery catheter and the packaging catheter are consistently aligned. Then image the markers on the test stent/device relative to the marker on the tip of the delivery catheter to determine what orientation (i.e., at what "hour" on the "clock") the stent needs to be loaded into the delivery catheter in order to achieve the desired orientation at the delivery site.

Optionally, the orientation can be confirmed with an additional test stent/device which is temporarily advanced in the predicted orientation, and then imaging can confirm, before the test device is removed and a permanent device is advanced and deployed.

By way of example, a test result shows a fenestration deploys at "7 o'clock", which is 90 degrees clockwise relative to the target branch vessel. The treatment would then reorient the stent-packaging catheter at "4 o'clock", to have it appear correctly oriented proximal to the target branch.

When a catheter tip orientation is imaged, the stent loaded in the appropriate orientation relative to the similarly disposed hub marker can be deployed. Once again, if desired, "test" device/stents with additional radio-opaque markers can be retrievably deployed to confirm the orientation.

Second Method

Disclosed is a second method, using the steps and markers of the above-described First Method, and in addition using a delivery catheter having throughout its cross section a unique geometrically shaped lumen. In atypical embodiment, the outer surface of the delivery catheter will be conventionally cylindrical, substantially rounded, to facilitate advancement through circulatory vessels. A non-round inner lumen minimizes the rotational tendency of a deploying stent-packaging catheter, or a wire, or a combination thereof, enhancing the predictability of orientation.

The accompanying figures show, by way of example, a triangularly shaped lumen. Alternatively, a square, hexagon, octagon, pentagon, a "house" silhouette, an oval, an ellipse, a star or other non-round shape. Any style of star may be used, such as 6-pointed, "Star of David" or others, provided a single one is used throughout the lumen.

In a further embodiment, the inner lumen of a packaging catheter may be shaped correspondingly to the shape of the lumen of the delivery catheter. This correspondence is shown in the accompanying FIGS. 1A and 1B, for example. This embodiment is configured such that the correspondingly shaped packaging catheter and delivery wire or hypotube are snug enough so as to not allow rotation, but loose enough to allow movement back and forth relative to one another. This embodiment will maintain a similar orientation through the advancement of the stent/device through the delivery catheter, allowing accurate and predicable deployment in appropriate and desired orientations.

Again here, a "12 O'clock" marker that is at the same orientation can be on the hub and on the catheter tip (radio-opaque on the catheter tip). So, when/if the catheter tip orientation is imaged, the stent loaded in the appropriate orientation relative to the similarly disposed hub marker can be used. It would typically be loaded on a delivery wire have a similar outer shape, to match the inner shape of the catheters. Once again, if desired, "test" device/stents with additional radio-opaque markers can be retrievably deployed to confirm the orientation.

In another example, a wire substantially of a non-round shape proximally, and extending all the way to the target zone in a continuous or nearly continuous fashion, is advanced via standard endovascular methods. The end of the wire, or the region where the non-round shape ends on the wire, would have a radio-opaque, or other marker that can be effectively imaged when in vivo, at the "12 o'clock" position of its circumference, with a matching "12 o'clock" marker on the proximal end of said wire, outside the patient's body. Most often multiple other distinct radiopaque markers, such as those of a different radio-density, shape or orientation, may also be present at the tip of the wire (or the catheter in the former examples). The relative position of the 12 o'clock marker can thereby be determined on a rotational basis, relative to a lesion and/or a branch orifice. Once the end marker and its relative rotation is visualized an appropriately oriented stent-loaded on a catheter with a similar and matching inner luminal shape as the outer surface of the wire, with the stent and optionally a balloon as well (on which the stent may be mounted) crimped down into a substantially similar shape-can then be loaded on the back of the wire, in a desired rotational orientation relative to the proximal 12 o'clock marker, as described above, can be loaded onto the wire, and delivered to the target area, whereupon the stent or other device can be deployed and implanted. Again, if desired, a test device may optionally first be deployed and then recaptured to confirm the rotational position at the target lesion. These matching substantially non-round wire and lumen configurations can be used in both over-the-wire as well as rapid-exchange configurations. In yet another example, the stent can be loaded inside a catheter with a substantially similar and matching inner lumen to the wire, and the stent preloaded into the catheter, and internally crimped into a similar shape, and may then be delivered. This would more commonly be used with self-expanding stents. With many self-expanding stents using the wire first method, there may be both an inner hypo-tube or catheter of an appropriate internal shape, a stent loaded on the outside of a section of said inner hypo-tube or catheter, and a second catheter or hypo-tube overlying the stent. The inner hypo-tube or catheter would be loaded onto the wire, and the outer hypo-tube would be retracted once the stent is at the target location, in order to release the external constraint of said stent and allow it to expand.

In another example, adapted optimally for many bifurcation lesions, the delivery catheter can have multiple lumens. In one example for the treatment of bifurcation narrowing, a substantially non-round wire can first be introduced into one branch, across one limb of the narrowing. The first stent can then be preloaded onto an appropriate balloon-mounted first catheter, with the first stent having a fenestration that will optimally be deployed at the origin of the second branch. The first lumen that extends from the end hole can either be a full-length lumen, extending from distal end-hole to proximal end hole, or can be a "rapid exchange" configuration, in which the primary wire lumen extends from the end hole to a proximal side hole. Another secondary lumen serves only to inflate and deflate the balloon on the primary catheter, with a fenestrated stent mounted on the balloon. The primary catheter, stent, and balloon in the currently described embodiment must all have a fenestration/distal side hole at the same overlapping side and segment. The distal side hole serves as the end hole for another tertiary lumen, which extends proximally along the entire intravascular course of the balloon inflation lumen, and branches from the balloon inflation lumen proximally, outside of the patient's body. In the over-the wire configuration there would be a third branch outside the body; the proximal extension of the primary lumen. In the preferred current embodiment in which the primary lumen has a rapid exchange configuration from the end-hole to the proximal side hole, the current embodiment can sometimes work in relatively straight and non-tortuous anatomy even with a round lumen and round wire—as a second wire can be advanced into the side branch, via the distal side hole and the proximal tertiary lumen, via its proximal end hole. In straight anatomy, advancing a wire through this lumen, out the distal side hole, and into the side branch may usually help align the entire construct and the pre-mounted primary stent into the appropriate configuration, with the fenestration at the side branch orifice. However, in most tortuous anatomy, the substantially non-round wire and inner lumen of the primary lumen will be necessary to properly preload the primary lumen in the desired configuration, so the fenestration faces the orifice of the side branch. Multiple fenestrations for multiple side branch orifices are possible as well. Additional radiopaque markers can mark the proximal and distal ends of the stent, as well as the proximal and distal ends of any fenestration. In the preferred current single fenestration, rapid exchange, substantially non-round wire and primary lumen configuration, a second wire can be advanced through the tertiary lumen and into the side branch before the primary balloon is inflated and the primary stent is deployed. The primary stent mounted on a delivery catheter can then be removed if desired, while leaving the second wire in place in the side branch. The primary wire can either be left in place or removed. A second stent, mounted on a second catheter, can then be advanced over the second wire and into the branch orifice, where it can then be deployed. If the second stent has fairly large interstices that would not significantly impede blood flow, then a typical round wire and second-stent catheter system can be used to develop and deploy a "y" configuration stent system at the bifurcation. If, however, there is a need and/or a desire to have an additional fenestration in the second stent overlying the branching-point origin of the primary distal branch, then the second wire should also be a substantially non-round wire, and a corresponding second catheter with a corresponding non-round lumen should be used, in order to appropriately align the fenestration in the second fenestrated stent device.

Common Method

Using any of the devices and methods above, a fenestration can be accurately deployed at the origin of a branch vessel. Then a wire can be advanced through that fenestration and into the branch, and either: (a) a balloon expandable device/stent can be delivered over the wire and deployed so that the proximal end minimally overlaps with the fenestration of the first stent/device; moreover, the branch may also optionally have a taper so it is somewhat larger at the fenestration side versus the portion that extends into the branch vessel; (b) a second delivery catheter (or the first can be re-used) can be delivered into the branch (the wire can optionally be removed) and an additional stent can be delivered through the delivery catheter. Again, the branch may also optionally have a taper so it is somewhat larger at the fenestration side versus the portion that extends into the branch vessel. Option (b) is currently the most common and preferred delivery method for this family of devices.

Delivery method (b), however, has difficulty accurately landing the proximal stent, especially with "woven" or "braided" stents which can significantly, and unpredictably, foreshorten during deployment (compared to their length crimped in the delivery catheter).

Another option therefore is a novel delivery device for such stents. In this embodiment, it can be loaded in a device/catheter similar to the "inner catheter with wings" of a filter-tip TAVR (transcatheter aortic valve replacement) catheter. The "wings" provide the outer constraint for the preloaded self-expanding stent, while the inner hypo-tube attached to the "wings" have an appropriate substantially non-round inner lumen to extend over a similar shaped wire in the desired orientation. The stent is loaded on an outer hypo-tube, preferably in the same non-round configuration. To deploy the stent in a proximal to distal fashion the stent inner hypo-tube and its attached "wings" are advanced, while the outer hypo-tube and the stent thereon are held in place, thus releasing the proximal part of the elf-expanding stent first, and still allowing potentially for the stent to be re-sheathable when partially deployed, by reversing the movements. When using a wire-first configuration of the inventions described herein, the larger the diameter of the wire, the less likely it is to rotate in an unwanted way during catheter delivery, while being guided through the angular lumen 1 of the delivery catheter. Alternative embodiments may have an additional anchor at the end of the wire. Examples of such anchors may include a coil, a spring, a multi-pronged wire ending, a retrievable stent and others.

Having a single or multiple external wire attached to a stent, in a preferred embodiment ideally attached to the proximal and distal ends of the stent (which can be "over the wire" or most ideally "rapid exchange") once the first advanced through the fenestration into the branch, the second stent/device is advanced over the wire to the desired position. The stent attached wires (or, alternatively, an outer catheter) is held in place while the "inner catheter with wings" is advanced, exposing/unsheathing the stent from the proximal end first.

The present invention also discloses an unsheathing device for the branch stent. More specifically the present invention teaches a device which un-sheaths the proximal part first. In the foregoing, if the stent is attached by wires, the wires can expand with the stent. If the stent is attached distally to an outer catheter (which is outside the inner catheter, but still inside the stent; the wings are outside the stent), it would need to wait until the entire stent is unsheathed before detaching the proximal end, if attached. However, in self-expanding non-attached stents, the stent would automatically expand and detach from a proximal to distal orientation at the inner catheter and its overlapping "wings" covering the stent are advanced, thereby releasing the stent progressively from the constraint of the "wings". Or if the stent is attached circumferentially proximally to an outer catheter and also has at least one additional wire attached to the stents distal segment- or additional attachment(s) to the outer catheter at the distal stent segment, then the proximal attachments can be detached upon unsheathing the proximal segment of the stent to ensure appropriate orientation and position overlapping the fenestration but not significantly overlapping/covering the primary vessel, and then the distal stent can be detached once the entire stent is deployed.

The stent can optimally be attached only distally to the "outer catheter", in order to advance the system, the outer catheter is pushed, which pulls the attached stent and pushes the winged portion of the inner catheter (and subsequently the entire inner catheter in unison). Then, when the stent is properly positioned, the second stent can be unsheathed by holding the outer catheter (with attached stent) in position and then advancing the inner catheter and its attached "wings", which will un-sheath the proximal stent first. Using self-expanding stents, the proximal stent will automatically expand as it is unsheathed. If the position is off, the inner catheter can be pulled back again and the proximal stent can be re-sheathed in versions that are partially of fully detachable distally, and the stent can be repositioned before unsheathing again.

In another embodiment, once the primary substantially non-round wire is advanced, a quaternary catheter, with both a corresponding substantially non-round inner lumen as well as a similar outer surface shape, with a proximal and distal "12 o'clock" marker, but without a hub, can first advanced, to help fix the rotational position of the wire. The primary wire and this quaternary catheter can then be used as the wire/rail to deliver the primary catheter in the desired configuration, with less chance of unwanted rotation during delivery and/or deployment of the primary stent.

Additionally, when using "braided" or "woven" stents, full expansion can be slow and unpredictable, the proximal end of stent (and optionally other parts as well) can have one or more nitinol wire rings to encourage more immediate opening/self-expansion to its maximal diameter, or to the vessel diameter, and maximize stent vessel wall apposition. There may optionally be similar attached longitudinal wires as well to help allow smooth re-sheathing when desired.

More particularly, a preferred method may be described by the following steps, using the embodiment of the device in which the pusher wire comprises an angular shape congruent with the angular lumen of the delivery catheter (e.g., a triangularly shaped pusher wire and triangular lumen):

(a) inserting said delivery catheter into a body,
(b) pushing said proximal end of said delivery catheter over any primary wire until said distal end of said delivery catheter is proximal to a target aneurysm,
(c) removing said primary wire
(d) orienting said packaging catheter with inner shaped pusher wire and pre-loaded stent in a set orientation relative to said port of said hub so as to set orientation of said stent relative to said target aneurysm,
(e) inserting said packaging catheter into said port of said hub,
(f) attaching said hub to said proximal end of said delivery catheter,
(g) pushing said pusher wire with said stent from said packaging catheter and into said delivery catheter until said stent is proximal to said target aneurysm,
(h) partially withdrawing said delivery catheter while holding or advancing said pusher wire, until said stent is fully exposed,
(i) deploying said differentially porous occlusion device,
(j) withdrawing said pusher wire, and
(k) withdrawing said delivery catheter.

Bifurcated or Y-Shaped Stents—Using the foregoing procedure, a "Y" shaped stent may be assembled from two stents in vivo by reference to markers. In the example above, once the first fenestrated occlusion device is deployed, a second delivery catheter, or optionally the first one can be reused, and can be advanced over any wire, through the proximal stent, through the fenestration, and into the side branch. Another second stent occlusion device can then be deployed. The second stent occlusion device can either have no fenestration, and be positioned so as to minimally overlap the edges of the fenestration of the first stent occlusion device at the proximal end of the deployed second stent occlusion device; or alternatively a second fenestrated device can be deployed in a similar fashion to the first to build a "Y" construct, with the methods described above used to ensure the secondary fenestration (on the second stent) properly overlaps the orifice of the primary vessel branch.

The present invention may employ self-expanding components.

The present invention may employ balloon-expanding components.

The present invention may optionally contain radiopaque components and/or radiopaque markers. These can be especially valuable at ends of stent and at the ends of covered or less porous zone, or to define a fenestration. Radio-opaque materials and markers can also be optionally present in more places, and sometimes throughout.

The present invention may have branched stent elements.

The present invention's stent elements may optionally be fully re-sheathable.

The present invention's stent elements may optionally be partly re-sheathable.

All stent elements of the present invention may be optionally be detachable.

The foregoing can also be applied to various endoscopic procedures as well. Additionally, it should be noted that in the preferred embodiment the stents are cylindrical when fully expanded and crimped down into a triangular (or other) shape, however, in some embodiments the stent itself is triangular (or other shape) but most vessels are cylinders.

The current invention can be used to similarly introduce other devices, such as contoured mesh sacs to fill an outpouching, in its preferred orientation. One of many examples of such an outpouching is a vascular aneurysm. In some embodiments this can allow custom implants to be made to contour to the shape of a particular lesion, and subsequent accurate orientation of delivery and deployment of said device.

The current system can also be used to deliver coated devices. Some examples of the many coatings that can be used include lubricious compounds, sticky compounds, hydrogels, pharmaceuticals, chemotherapeutic agents, cells, proteins, combinations of these coatings, and others. Coatings may be on the inner surface, the outer surface, the interstices, and combinations thereof.

The current system may also be further combined with the multiple circumferential balloon catheter previously described by Walzman (US 2020/10,543,015) for additional precision in positioning the tip of said delivery catheter in a desired radial position with a vessel, an aneurysm, or the neck of an aneurysm, for optimal safety and accuracy of device delivery.

It will be understood by those skilled in the art that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

What is claimed is:

1. An intravascular device comprising:
    (a) a delivery catheter having a proximal end, a distal end, a fixed non-round shaped inner lumen, a proximal hub with a marker, a corresponding marker at said distal end of said delivery catheter, said delivery catheter capable of:
        (i) moving within a blood vessel to a target lesion;
        (ii) stopping proximal to the target lesion; and
        (iii) withdrawing from the blood vessel;
    (b) a packaging catheter with a fixed non-round shaped inner lumen, corresponding to said inner lumen of said delivery catheter, a pusher wire having a proximal end, a distal end, and an occlusion device releasably disposed on said distal end of said pusher wire, preloaded into said packaging catheter at a fixed circumferential orientation, with one or more corresponding markers on an outer surface of said packaging catheter;
    (c) said hub having an inner lumen that is shaped to receive said distal end of said packaging catheter in one of at least two different fixed orientations, said distal end of said packaging catheter being adapted to deliver said distal end of said pusher wire into said inner lumen of said delivery catheter;
    (d) said pusher wire comprising an outer shape corresponding to said inner lumen of said delivery catheter, and configured such that, with said occlusion device loaded thereon, said occlusion device is capable of slidable passage through said inner lumen of said delivery catheter, wherein said pusher wire substantially maintains said orientation relative to said delivery catheter during movement of said distal end of said delivery wire through the blood vessel to the target lesion; and
    (e) said packaging catheter further being capable of being rotated prior to reception within said hub of said delivery catheter so that said pusher wire and said occlusion device therein are rotated simultaneously by the same amount, whereupon said pusher wire and said occlusion device can be advanced into said delivery catheter into a predicted orientation of said occlusion device, and maintain said orientation during advancement thereof through said delivery catheter, and while said delivery catheter is withdrawn.

2. The device according to claim 1, wherein said occlusion device is a stent.

3. The device according to claim 2, wherein said stent is differentially porous.

4. The device according to claim 3, wherein said stent comprises at least one fenestration.

5. The device according to claim 4, wherein said stent comprises at least one region that is substantially impermeable to fluid.

6. The device according to claim 2, wherein said stent comprises at least one region that is substantially impermeable to fluid.

7. The device according to claim 2, further comprising at least one adhered compound.

8. The device according to claim 2, further comprising a lubricious surface coating.

9. The device according to claim 1, wherein said occlusion device is an asymmetric shaped disc with at least one adhered coil wire.

10. The device according to claim 1 wherein said occlusion device is an asymmetrically shaped disc.

11. The device according to claim 10, wherein said pusher wire is a hypotube.

12. The device according to claim 10, further containing at least one adhered compound.

13. The device according to claim 12, wherein said at least one adhered compound is a hydrogel.

14. The device according to claim 1, wherein said occlusion device is a mesh sac.

15. The device according to claim 14, further containing at least one adhered compound.

16. The device according to claim 15, wherein said at least one adhered compound is a hydrogel.

17. The device according to claim 1, wherein said delivery catheter includes at least one radio-opaque marker along a segment of said delivery catheter.

18. The device according to claim 17, wherein said at least one radio-opaque marker is the marker on the distal end of said delivery catheter.

19. The device according to claim 1, including at least one radio-opaque marker along said pusher wire.

20. The device according to claim to claim 1, wherein said occlusion device comprises at least one radio-opaque marker.

21. The device according to claim 1, wherein said outer shape of said pusher wire is congruent with said inner lumen of said delivery catheter, said outer shape of said pusher wire and said inner lumen of said delivery catheter each defining an angular profile.

22. The device according to claim 1, wherein said non-round shapes of said inner lumens of said delivery catheter and said packaging catheter and said outer shape of said pusher wire are each non-angular.

23. The device according to claim 9, wherein said pusher wire is a hypotube.

24. A method of using the device of claim 1 to form a Y configured occlusion construct, comprising the steps of:
  (a) inserting said delivery catheter into a body over a primary wire,
  (b) pushing said proximal end of said delivery catheter until said distal end of said delivery catheter is proximal to a target aneurysm, and in a primary branch distal to a vessel bifurcation,
  (c) removing said primary wire,
  (d) using imaging to record the orientation of said marker at said distal end of said delivery catheter and the degrees of its rotation relative to said marker at said proximal hub,
  (e) orienting said packaging catheter relative to said hub so as to orient said occlusion device which is a stent, with a fenestration such that said fenestration is oriented to overlie an orifice of a secondary branch arising from the bifurcation, relative to the target aneurysm,
  (f) inserting said packaging catheter into said hub,
  (g) pushing said pusher wire from said packaging catheter and into said delivery catheter, and pushing said pusher wire until said stent is proximal to the target aneurysm, and said fenestration is properly aligned to overlap the orifice of the secondary branch, utilizing imaging guidance,
  (h) withdrawing a portion of said delivery catheter, while advancing said pusher wire, until said stent is substantially partially unsheathed,
  (i) using imaging to confirm orientation and positioning of said stent,
  (j) withdrawing a portion of said delivery catheter, while advancing said pusher wire, until said stent is fully unsheathed and fully detached,
  (k) withdrawing said pusher wire,
  (l) advancing said delivery catheter over a secondary wire, through said stent, and through said fenestration of said stent, and into the secondary branch,
  (m) removing said secondary wire,
  (n) using imaging to record the orientation of said marker at said distal end of said delivery catheter and the degrees of its rotation relative to said marker at the proximal hub,
  (o) orienting a secondary packaging catheter relative to said hub so as to orient a secondary stent with a fenestration oriented to overlie the orifice of the primary branch arising from the bifurcation, relative to the target aneurysm,
  (p) inserting said secondary packaging catheter into said hub,
  (q) pushing a secondary pusher wire from said secondary packaging catheter and into said delivery catheter, and pushing said secondary pusher wire until said secondary steut is proximal to the target aneurysm, and said fenestration of said secondary stent is properly aligned to overlap the orifice of the primary branch, utilizing imaging guidance,
  (r) withdrawing a portion of said delivery catheter, while advancing said secondary pusher wire, until said secondary stent is substantially partially unsheathed,
  (s) using imaging to confirm orientation and positioning of said secondary stent,
  (t) withdrawing a portion of said delivery catheter, while advancing said secondary pusher wire, until said secondary stent is fully unsheathed and fully detached,
  (u) removing said secondary pusher wire, and
  (v) removing said delivery catheter.

25. A method of using the device of claim 1, comprising the steps:
  (a) inserting said delivery catheter into a body over a primary wire,
  (h) pushing said proximal end of said delivery catheter until said distal end of said delivery catheter is proximal to a target aneurysm,
  (c) removing said primary wire,
  (d) using imaging to record the orientation of said marker at said distal end of said delivery catheter and the degrees of its rotation relative to said marker at said proximal hub,
  (e) orienting said packaging catheter relative to said hub so as to orient said occlusion device which is a stent relative to said target aneurysm,
  (f) inserting said packaging catheter into said hub,
  (g) pushing said pusher wire from said packaging catheter and into said delivery catheter, and pushing said pusher wire until said stent is proximal to said target aneurysm utilizing imaging guidance,
  (h) withdrawing a portion of said delivery catheter, while advancing said pusher wire, until said stent is substantially partially unsheathed,
  (i) using imaging to confirm orientation and positioning of said stent,
  (j) withdrawing a portion of said delivery catheter, while advancing said pusher wire, until said stent is fully unsheathed and fully detached when orientation and positioning is confirmed,
  (k) withdrawing said pusher wire, and
  (l) withdrawing said delivery catheter.

* * * * *